US009730653B2

(12) United States Patent
Niizeki et al.

(10) Patent No.: US 9,730,653 B2
(45) Date of Patent: Aug. 15, 2017

(54) X-RAY CT APPARATUS

(71) Applicant: J. MORITA MANUFACTURING CORPORATION, Kyoto-shi (JP)

(72) Inventors: Ryuichiro Niizeki, Kyoto (JP); Hideki Yoshikawa, Kyoto (JP); Susumu Kirimura, Kyoto (JP)

(73) Assignee: J. MORITA MANUFACTRING CORPORATION, Kyoto-Shi (JP)

( * ) Notice: Subject to any disclaimer, the term of this patent is extended or adjusted under 35 U.S.C. 154(b) by 192 days.

(21) Appl. No.: 14/573,459

(22) Filed: Dec. 17, 2014

(65) Prior Publication Data

US 2015/0164441 A1 Jun. 18, 2015

(30) Foreign Application Priority Data

Dec. 18, 2013 (JP) .................. 2013-261364

(51) Int. Cl.
*A61B 6/03* (2006.01)
*H05G 1/02* (2006.01)
*A61B 6/00* (2006.01)

(52) U.S. Cl.
CPC ............ *A61B 6/035* (2013.01); *A61B 6/4405* (2013.01); *A61B 6/4441* (2013.01); *H05G 1/02* (2013.01)

(58) Field of Classification Search
CPC .. A61B 6/00; A61B 6/03; A61B 6/032; A61B 6/035; A61B 6/44; A61B 6/4405; A61B 6/4429; A61B 6/4435; A61B 6/4441; H05G 1/02

USPC .............. 378/4, 15, 193, 195, 196, 197, 198
See application file for complete search history.

(56) References Cited

U.S. PATENT DOCUMENTS

| 6,132,087 A | 10/2000 | Kusch et al. |
| 7,073,940 B2 * | 7/2006 | Saladin .................... A61B 6/56 378/193 |
| 8,422,628 B2 | 4/2013 | Niizeki |
| 2007/0121790 A1 | 5/2007 | Grady |
| 2012/0257725 A1 | 10/2012 | Noda |
| 2012/0300909 A1 | 11/2012 | Simmons et al. |
| 2013/0243166 A1 | 9/2013 | Moulin et al. |

FOREIGN PATENT DOCUMENTS

| JP | 11-192220 | 7/1999 |
| JP | P2007-159987 A | 6/2007 |
| JP | 2011-25012 A | 2/2011 |
| JP | P2012-61305 A | 3/2012 |
| JP | 2013-17818 A | 1/2013 |
| WO | WO 2010/078481 A1 | 7/2010 |

\* cited by examiner

*Primary Examiner* — Jurie Yun
(74) *Attorney, Agent, or Firm* — DLA Piper LLP (US)

(57) ABSTRACT

An X-ray CT apparatus including an X-ray generator, an X-ray detector, a support part, and a base that rotatably supports the support part. The support part includes an exterior part made of carbon fiber reinforced plastic, and the X-ray generator and the X-ray detector are supported by the exterior part while being opposed to each other. The base rotatably supports the support part such that the X-ray generator and the X-ray detector turn about a turning axis.

8 Claims, 7 Drawing Sheets

X-RAY CT APPARATUS

BACKGROUND OF THE INVENTION

Field of the Invention

The present invention relates to an X-ray CT apparatus, particularly to a structure suitable for the X-ray CT apparatus in which a turning axis for an X-ray generator and an X-ray detector are horizontally arranged.

Description of the Background Art

For example, Japanese Patent Application Laid-Open No. 2011-025012 discloses an X-ray CT apparatus provided with a support arm that supports an X-ray source and an X-ray detector while the X-ray source and the X-ray detector are opposed to each other. The support arm includes a pair of arms that are supported in a cantilever manner while separated from each other, and an outline of the support arm is formed into substantially a U-shape as a whole. The support arm is arranged so as to be able to rotate about a horizontally-provided rotating axis. In the X-ray CT apparatus of Japanese Patent Application Laid-Open No. 2011-025012, the X-ray source and the X-ray detector turn about an affected area by rotating the support arm, thereby performing CT photography.

Japanese Patent Application Laid-Open No. 2013-017818 discloses an imaging apparatus provided with an image capturing assembly in which an X-ray tube and an X-ray detector are arranged at two ends of an arc arm while opposed to each other. In the imaging apparatus of Japanese Patent Application Laid-Open No. 2013-017818, a tubular pole made of carbon fiber is used as a mechanical link used in a position determination system.

SUMMARY OF THE INVENTION

In Japanese Patent Application Laid-Open Nos. 2011-025012 and 2013-017818, it is conceivable that the X-ray source and the X-ray detector are supported by a frame made of steel, or the like.

In an actual product, a support member constituting a parent body supporting an X-ray source and an X-ray detector is constructed with a frame having a steel structure, and the whole frame to which the X-ray source and the X-ray detector are fixed is covered with a thin resin or sheet-metal exterior member having no support function.

In X-ray CT photography, in order to obtain an accurate CT image, it is preferable that the turning axis for the X-ray source and X-ray detector is kept as stable as possible. Rigidity enhancement of the frame supporting the X-ray source and the X-ray detector is effective to eliminate wobbling of the turning axis. However, it is necessary to thicken and strengthen the frame made of steel, which results in a problem in that the weight of the frame increases. When the weight of the frame increases, it is also necessary to use a reinforcement structure for a mechanism rotatably supporting the frame, which results in a further problem in that the weight of the X-ray CT apparatus increases.

Thus, the problem that the turning axis for the X-ray source and the X-ray detector is kept as stable as possible and the problem that the weight reduction of the X-ray CT apparatus is achieved are contradictory, and it is difficult to simultaneously solve these problems in the structure in which the X-ray source and the X-ray detector are supported by the steel frame.

An object of the present invention is to restrain the wobble of the turning axis for the X-ray generator and X-ray detector and reduce the weight of the X-ray CT apparatus.

The objects underlying the present invention are achieved by the subject-matter of the independent claims. Preferred embodiments are defined in the dependent claims.

In accordance with a first aspect of the present invention, an X-ray CT apparatus includes: an X-ray generator; an X-ray detector; a support part that includes an exterior part made of carbon fiber reinforced plastic, the support part supporting the X-ray generator and the X-ray detector while the X-ray generator and the X-ray detector are opposed to each other using the exterior part; and a base that rotatably supports the support part such that the X-ray generator and the X-ray detector turn about a turning axis.

In the X-ray CT apparatus, the exterior part itself has a function of supporting the X-ray generator and the X-ray detector. The X-ray CT apparatus according to one aspect of the present invention differs from the conventional technology according to which the exterior member is required in addition to the member supporting the X-ray generator and the X-ray detector in this point. The weight of the carbon fiber reinforced plastic itself is light, and a space is formed in the exterior part, so that a weight reduction of the support part including the exterior part can be achieved. The weight of the structure rotatably supporting the support part can also be reduced. Therefore, the weight of the whole X-ray CT apparatus can be reduced.

The carbon fiber reinforced plastic has an excellent strength, and a structural portion supporting the X-ray generator and the X-ray detector is formed into a shape constituting the exterior part, which allows the structure having excellent rigidity to be implemented. The weight of the support part, which includes the exterior part, is thus reduced, and the rigidity of the support part is enhanced, which allows the restraint of the wobble of the turning axis for the X-ray generator and X-ray detector. Therefore, the wobble of the turning axis for the X-ray generator and X-ray detector can be restrained, and the weight of the X-ray CT apparatus can be reduced.

In accordance with a second aspect of the present invention, in the X-ray CT apparatus according to the first aspect, the base supports the support part such that the turning axis is horizontal.

When the turning axis is horizontally provided, the wobble of the turning axis is easily generated because gravity application directions of the X-ray generator and the X-ray detector vary about the horizontal turning axis. According to the second aspect of the present invention, therefore, in the structure of the horizontal turning axis, the effect that the weight reduction of the X-ray CT apparatus is achieved while the wobble of the turning axis for the X-ray generator and X-ray detector is restrained can significantly be exerted by using the support part, which is provided with the exterior part made of carbon fiber reinforced plastic, wherein the exterior part supports the X-ray generator and the X-ray detector such that the X-ray generator and the X-ray detector are opposed to each other.

In accordance with a third aspect of the present invention, in the X-ray CT apparatus according to the second aspect, the exterior part includes a pair of arms extending along the turning axis, and the X-ray generator and the X-ray detector are supported by the pair of arms while being opposed to each other.

The X-ray generator and the X-ray generator are thus supported by the pair of arms while being opposed to each other, so that the X-ray CT apparatus can be made compact.

In accordance with a fourth aspect of the present invention, in the X-ray CT apparatus according to the third aspect, the support part includes a turning support shaft part that is provided on an opposite side to the X-ray generator and the X-ray detector along the turning axis, and the base includes a seat and a turning support base part that rotatably supports the turning support shaft part above the seat to support the support part in a cantilever manner.

According to the fourth aspect of the present invention, because of the light support part, the support structure for the support part can be simplified even if the support part is rotatably supported in the cantilever manner.

In accordance with a fifth aspect of the present invention, in the X-ray CT apparatus according to the fourth aspect, the exterior part includes an arm base part that supports the pair of arms in a parallel state, the arms being opposed to each other with the turning axis interposed therebetween, the exterior part is formed into a tubular shape in which the pair of arms and the arm base part are continuously provided so as to form a U-shape, a generator-side opening is formed in one of the pair of arms in order to accommodate the X-ray generator in the generator-side opening, a detector-side opening is formed in the other of the pair of arms while opposed to the generator-side opening, the X-ray detector in an accommodated state being attached to the detector-side opening, and the turning support shaft part is attached to the exterior part so as to extend onto an opposite side to the pair of arms along the turning axis.

Therefore, a compact structure can be achieved while the X-ray generator and the X-ray detector are attached to the exterior part.

In accordance with a sixth aspect of the present invention, the X-ray CT apparatus according to the fourth or the fifth aspect further includes: a Y-direction moving mechanism configured to move the turning support base part in a Y-direction along a vertical direction; and a ZX-direction moving mechanism configured to move the turning support base part in a Z-direction along the turning axis and an X-direction orthogonal to both the Y-direction and the Z-direction together with the Y-direction moving mechanism.

Therefore, the support part, the X-ray generator, and the X-ray detector can be moved in a three-dimensional direction by the Y-direction moving mechanism and the ZX-direction moving mechanism, and the degree of freedom of an X-ray irradiation field of the X-ray generator can be enhanced. Because of the light support part, the support part itself places a small burden on the Y-direction moving mechanism and the ZX-direction moving mechanism.

The ZX-direction moving mechanism moves the turning support base part in the ZX-direction together with the Y-direction moving mechanism, so that miniaturization and weight reduction can be achieved in a portion that is elevated in the Y-direction.

In accordance with a seventh aspect of the present invention, the X-ray CT apparatus according to any one of the fourth to the sixth aspects further includes a turning drive part that is constructed with a hollow motor including a hollow rotating shaft part. At this point, the turning drive part is fixed to the turning support base part, the hollow rotating shaft part is coupled to the turning support shaft part, and the turning support shaft part is rotatably supported with a bearing interposed therebetween at a position separated from the turning drive part along the turning axis.

When the turning drive part is constructed with the hollow motor, a turning angle of the support part can accurately be controlled. The wobble of the turning axis can be restrained because the turning support shaft part is rotatably supported at the position distant from the turning drive part along the turning axis while the bearing is interposed between the turning axis and the turning support shaft part.

In accordance with an eighth aspect of the present invention, in the X-ray CT apparatus according to the seventh aspect, a plurality of bearings are provided, and the plurality of bearings are provided along the turning axis while separated from each other.

Therefore, the plural bearings are provided while separated from each other along the turning axis, so that the wobble of the turning axis can be restrained.

In accordance with a ninth aspect of the present invention, the X-ray CT apparatus according to the seventh or the eighth aspect further includes: an accommodation part that is provided on the turning axis while opened towards the pair of arms, at least a part of a subject being able to be accommodated in the accommodation part; and an accommodation part support part that is arranged through an internal space of the turning support shaft part, one end of the accommodation part support part being fixed to the accommodation part while the other end is fixed to the turning support base part. At this point, a cavity part is formed along the turning axis in the arm base part, and the turning support shaft part is formed into a hollow shape.

Therefore, the accommodation part that accommodates at least part of the subject therein can simply and compactly be fixed.

These and other objects, features, aspects and advantages of the present invention will become more apparent from the following detailed description of the present invention when viewed in conjunction with the accompanying drawings.

DESCRIPTION OF THE PREFERRED EMBODIMENT

Figure 1:
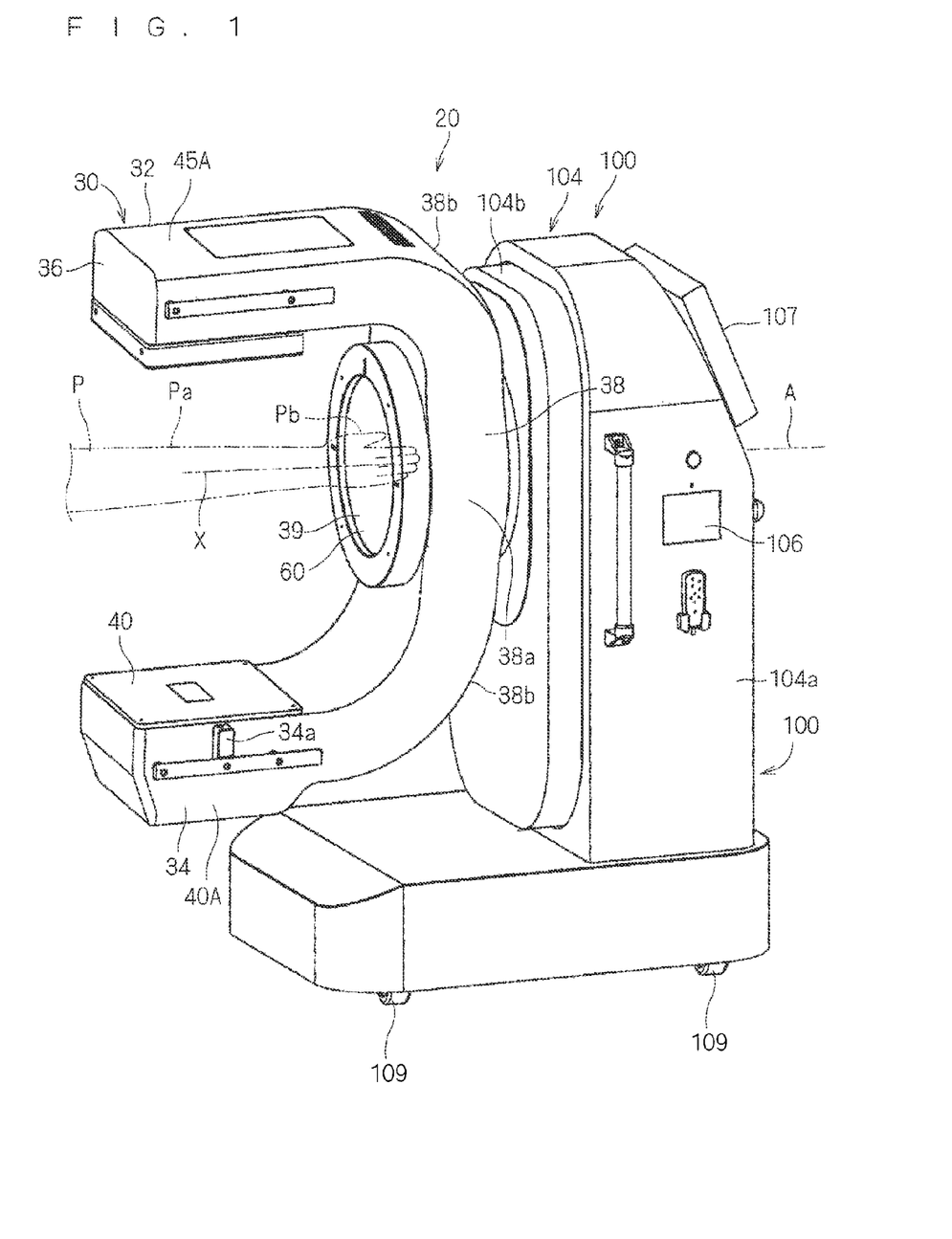
FIG. 1 is a perspective view illustrating an X-ray CT apparatus according to a preferred embodiment.
Figure 2:
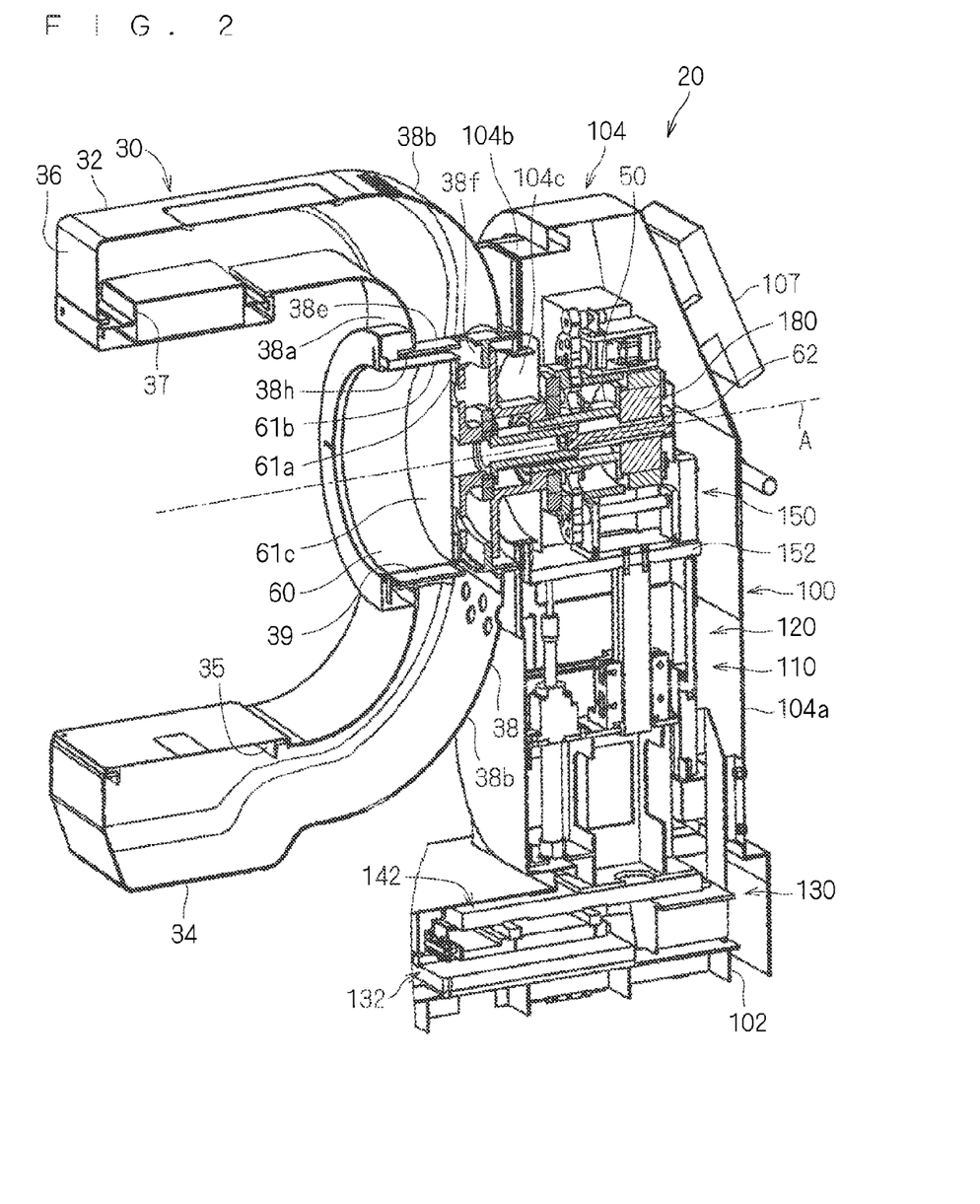
FIG. 2 is a sectional view illustrating an internal structure of the X-ray CT apparatus.
Figure 3:
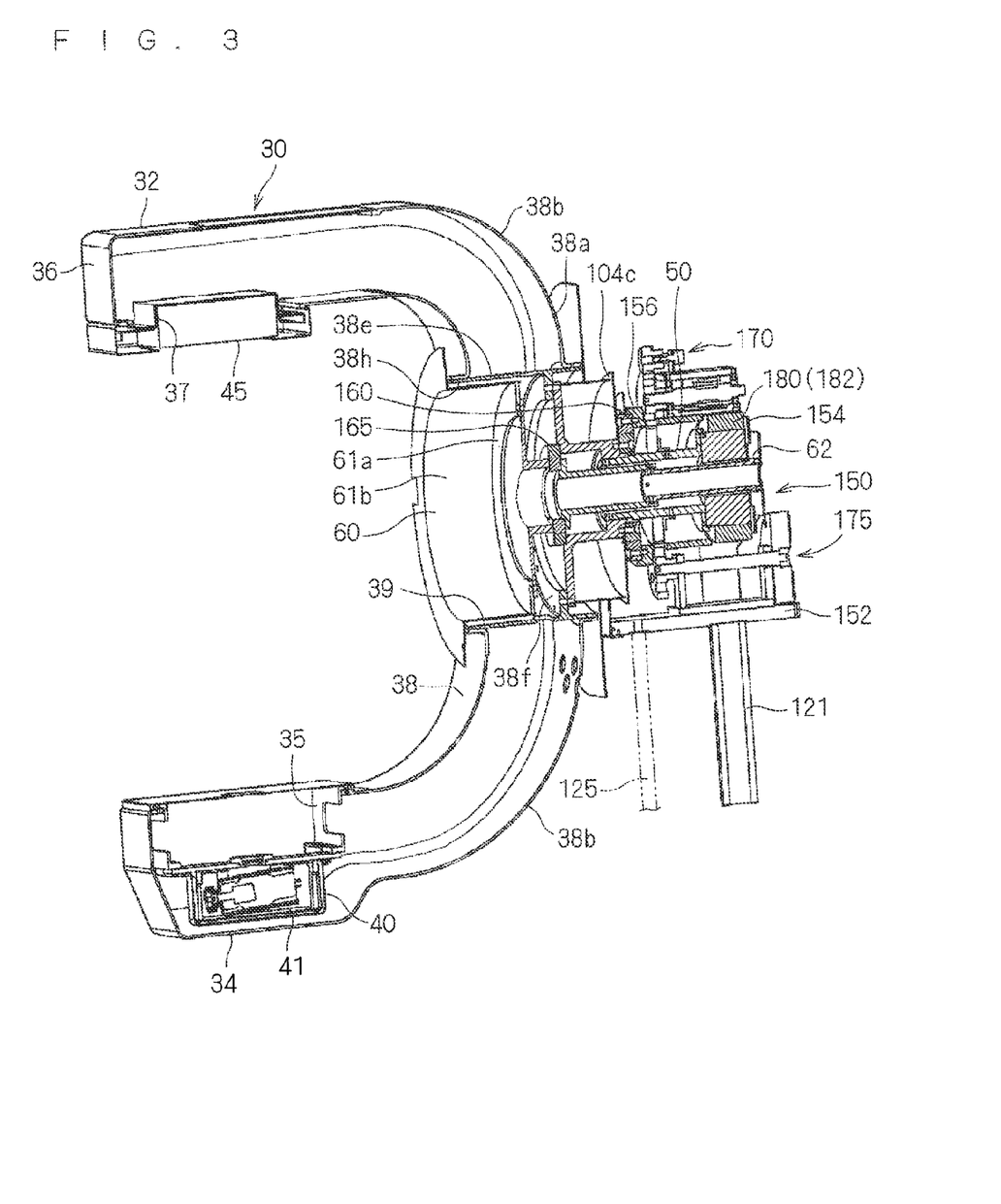
FIG. 3 is a sectional view illustrating a support part and a structure portion supporting the support part.
Figure 4:
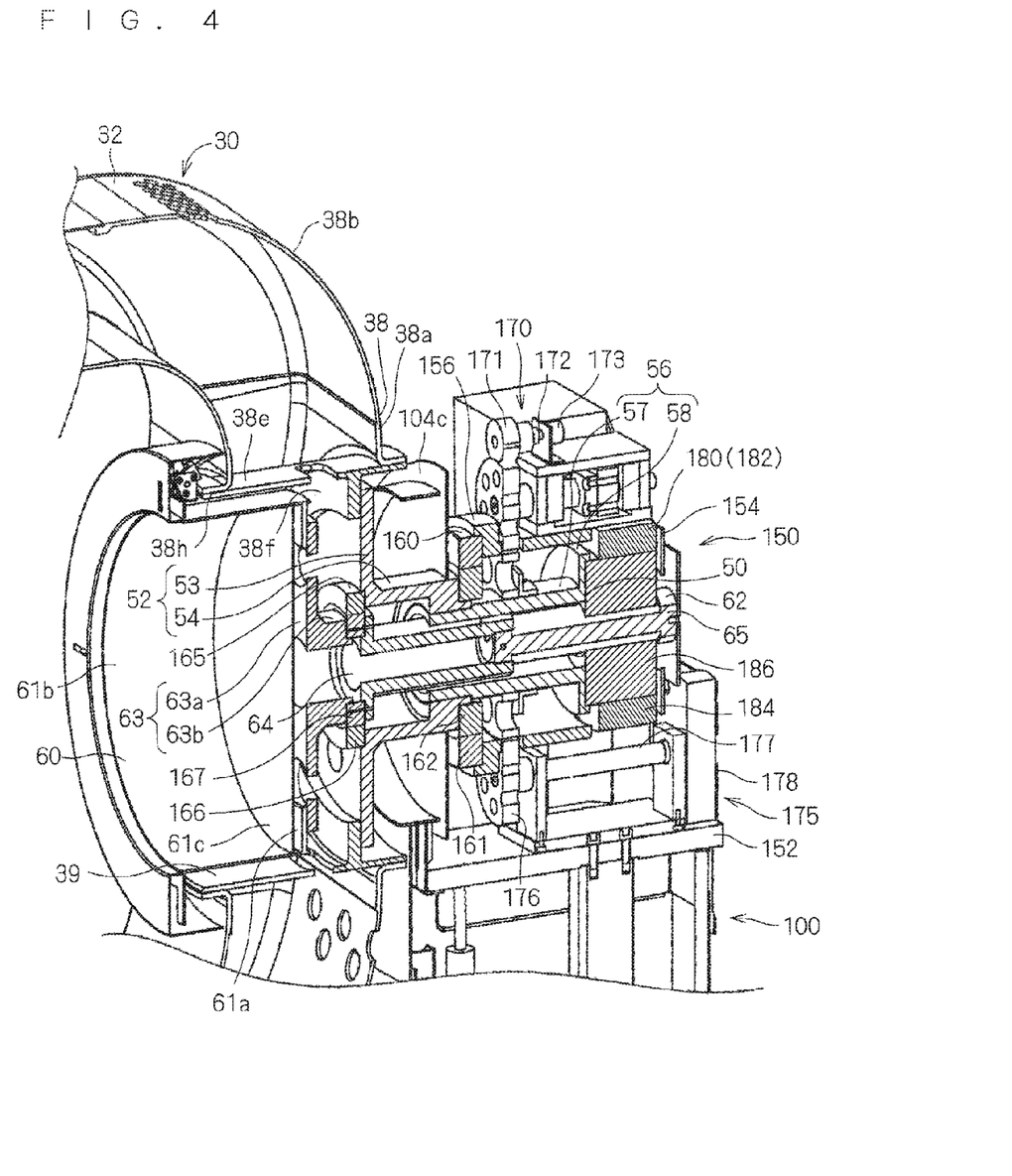
FIG. 4 is a sectional view illustrating the structure portion supporting the support part.
Figure 5:
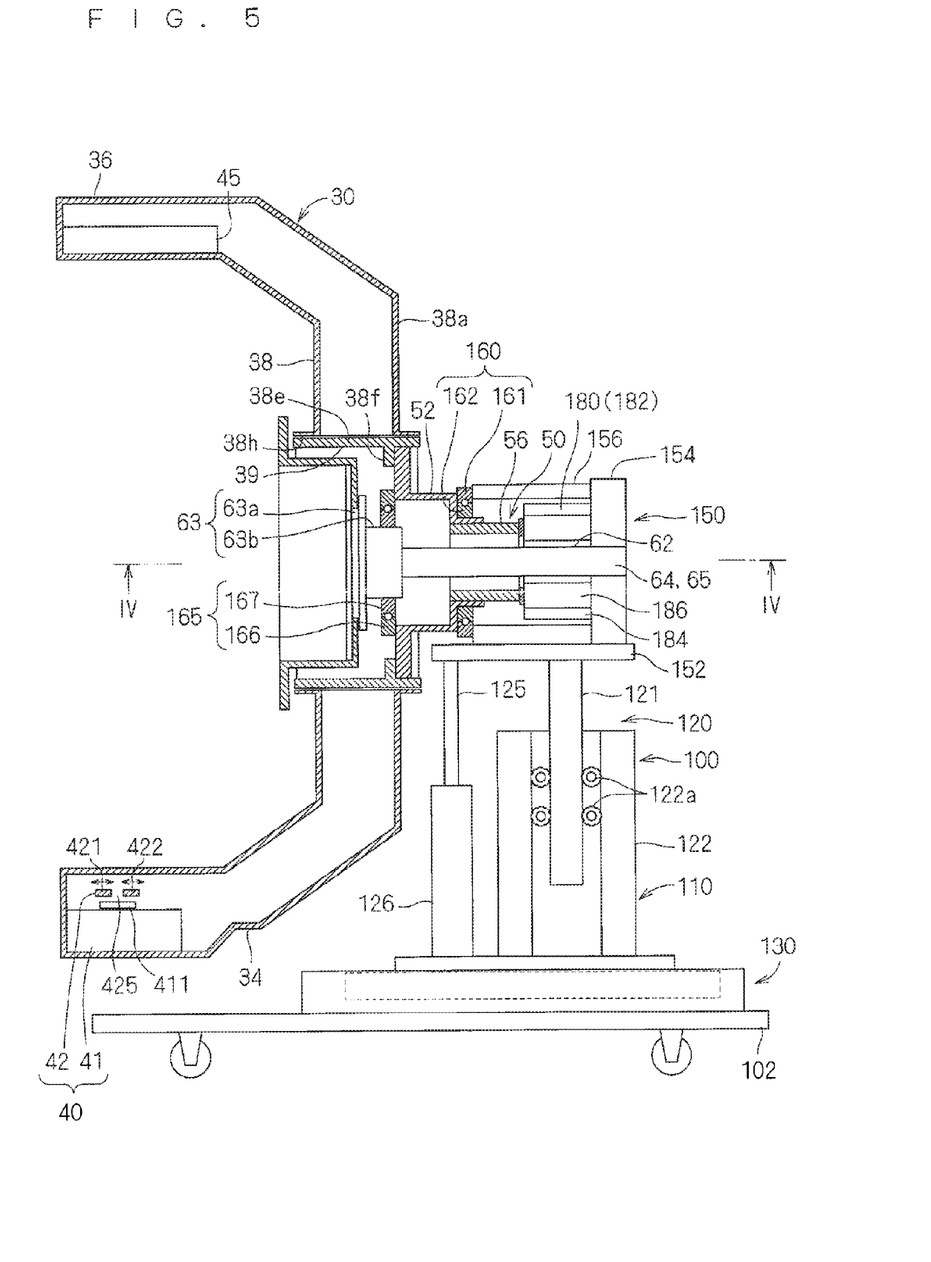
FIG. 5 is a schematic sectional view of the X-ray CT apparatus.
Figure 6:
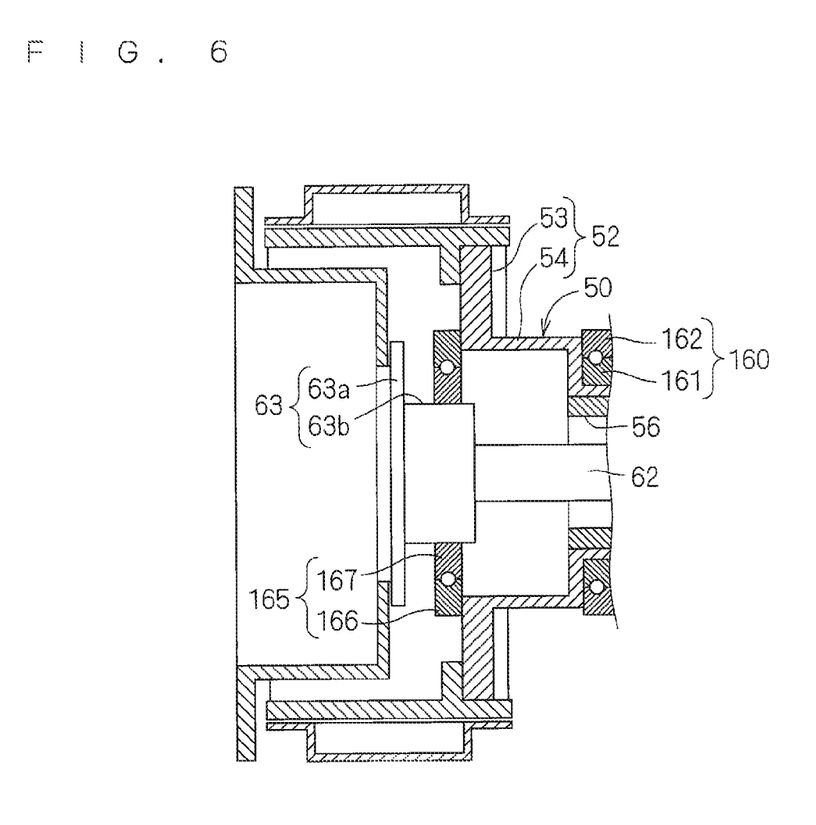
FIG. 6 is a schematic partially sectional view taken on a line IV-IV in FIG. 5.
Figure 7:
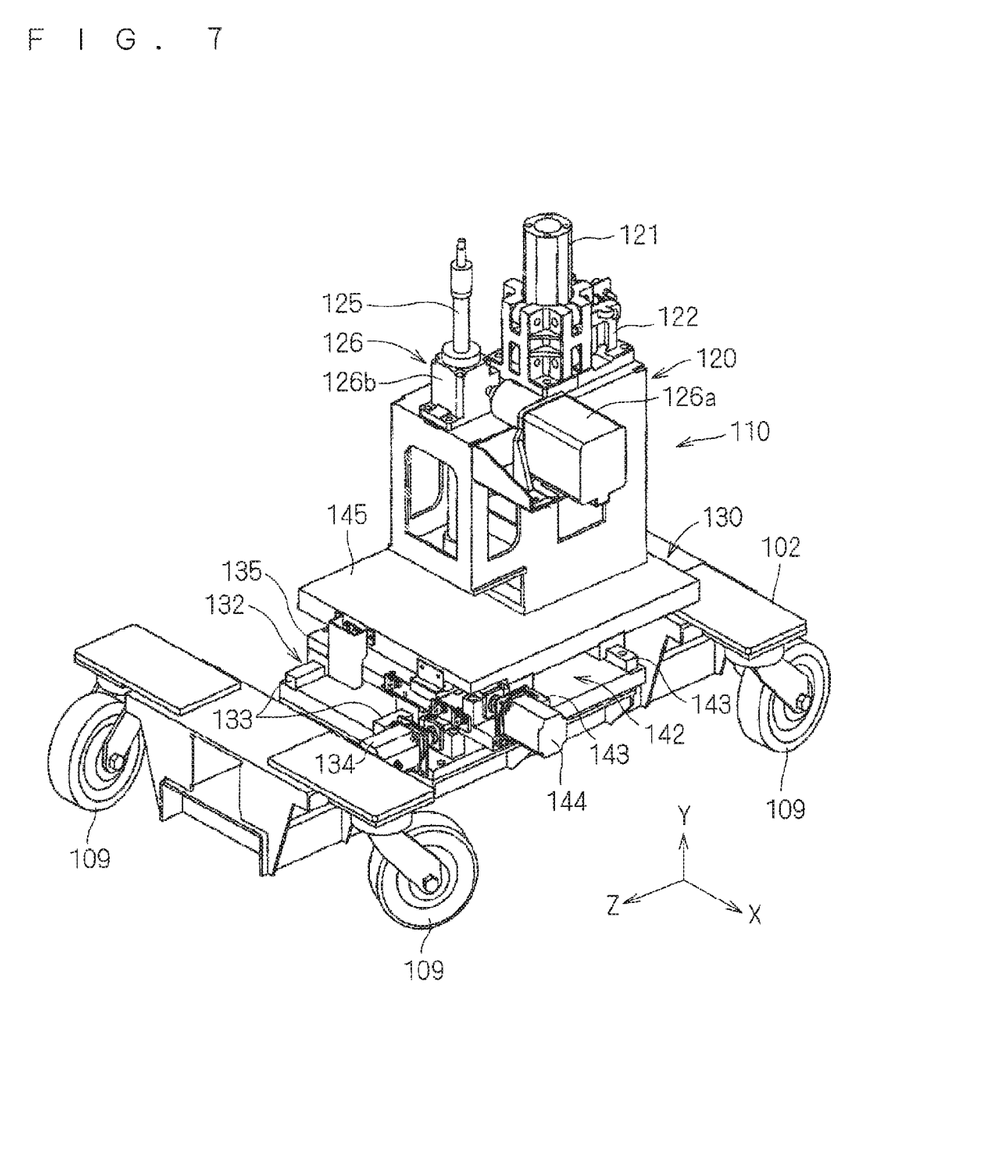
FIG. 7 is a perspective view illustrating a structure portion moving the support part in X-, Y-, and Z-directions.

An X-ray CT apparatus according to a preferred embodiment will be described below. FIG. 1 is a perspective view illustrating an X-ray CT apparatus 20, FIG. 2 is a sectional view illustrating an internal structure of the X-ray CT apparatus 20, FIG. 3 is a sectional view illustrating a support part and a structure portion supporting the support part, and FIG. 4 is a sectional view illustrating the structure portion supporting the support part. FIG. 5 is a schematic sectional view of the X-ray CT apparatus, and FIG. 6 is a schematic partially sectional view taken on a line IV-IV in FIG. 5. Since FIGS. 5 and 6 are schematic views for the purpose of the description of a relationship among parts, sometimes the part illustrated in another view is simplified or eliminated. FIG. 7 is a perspective view illustrating a structure portion moving the support part in X-, Y-, and Z-directions.

1. Entire Structure

An entire structure of the X-ray CT apparatus 20 will be described with reference to FIGS. 1, 2, and 5.

The X-ray CT apparatus 20 performs CT photography of parts, such as a head, a cervical spine, an arm joint, a hand finger, a breast, a lumber spine, a hip joint, a knee, and a leg, of a patient as a subject P. The X-ray CT apparatus 20 includes an X-ray generator 40, an X-ray detector 45, a support part 30, and a base 100.

The X-ray generator 40 can emit an X-ray cone beam. The X-ray detector 45 detects an X-ray, which is emitted from the X-ray generator 40 and transmitted through the subject P that is of a photographing target.

The support part 30 includes an exterior part 32 made of carbon fiber reinforced plastic, and the X-ray generator 40 and the X-ray detector 45 are supported by the exterior part 32 while being opposed to each other.

Each part constituting the X-ray CT apparatus 20 is directly or indirectly assembled in the base 100. The base 100 rotatably supports the support part 30 such that the X-ray generator 40 and the X-ray detector 45 turn about a turning axis A. Hereinafter, for the sake of convenience, sometimes the side on which the support part 30 is provided is referred to as a front side with respect to the base 100, and an opposite side to the front side is referred to as a rear side with respect to the base 100.

In the preferred embodiment, the base 100 supports the support part 30 such that the turning axis A is horizontally provided. For this reason, the X-ray generator 40 and X-ray detector 45 supported by the support part 30 are arranged with a gap while opposed to each other in relation to the turning axis A provided in the horizontal direction orthogonal to a vertical direction, and the X-ray generator 40 and X-ray detector 45 turn about the turning axis A. It is not necessary that the turning axis A be strictly horizontally arranged. For example, assuming that Szx is a horizontally expanding two-dimensional plane, that Da is an axial direction of the turning axis A, and that Aa is a minimum angle formed between the axial direction Da and the two-dimensional plane Szx, the minimum angle Aa may range from +20° to −20°, preferably the minimum angle Aa is zero. Although not illustrated, the turning axis A may mechanically be tilted to temporarily set the minimum angle Aa to zero. In this case, the turning axis A is also horizontally arranged.

In the X-ray CT apparatus 20, the X-ray CT photography of the subject P is performed as follows. The subject P is arranged between the X-ray generator 40 and the X-ray detector 45 along the turning axis A from the opposite side of the base 100. At this point, the support part 30 rotates about the turning axis A, to rotate the X-ray generator 40 and the X-ray detector 45 about the turning axis A. Based on an electric signal obtained by the X-ray detector 45, calculation processing of reconstructing a CT image of the subject P is performed to generate the CT image of the subject P.

Therefore, the X-ray CT apparatus 20 is configured as an apparatus that is suitable to perform X-ray CT photography while the subject P is horizontally arranged. The support part may be supported while being turnable about the turning axis tilted with respect to the horizontal direction or the turning axis along the vertical direction.

Each part will more specifically be described below.

2. Structure of Support Part

As illustrated in FIGS. 1 to 5, the support part 30 includes the exterior part 32. The exterior part 32 supports the X-ray generator 40 and the X-ray detector 45 while the X-ray generator 40 and the X-ray detector 45 are opposed to each other and are accommodated therein. The exterior part 32 can cover and protect the X-ray generator 40, the X-ray detector 45, and wiring materials connected to the X-ray generator 40 and the X-ray detector 45.

The exterior part 32 is made of carbon fiber reinforced plastic (CFRP). The carbon fiber reinforced plastic is light compared to metallic material such as steel, and also has excellent strength. The exterior part 32 supports the X-ray generator 40 and the X-ray detector 45 while accommodating the X-ray generator 40 and the X-ray detector 45 therein, weight reduction of the support part 30 including the exterior part 32 can be achieved. As a result of the weight reduction of the support part 30, the weight of a structural portion (to be described) that rotatably supports the support part 30 can be reduced. Therefore, a weight of the whole X-ray CT apparatus 20 can be reduced.

It is conceivable that the exterior part 32 is made of carbon fiber reinforced plastic in many ways. The exterior part 32 may be formed by bonding cloth woven with carbon fibers to plastic, or the exterior part 32 may be formed by uniformly dispersing and mixing fine pieces of carbon fibers in plastic.

The structural portion supporting the X-ray generator 40 and the X-ray detector 45 is made of carbon fiber reinforced plastic having excellent rigidity. The structural portion is formed into a shape corresponding to the exterior part 32, and a sectional shape in a surface orthogonal to the extending direction of the structural portion is formed into an annular shape (preferably box shape). Thereby excellent rigidity is obtained. The weight of the support part 30 including the exterior part 32 is reduced, and the rigidity of the support part 30 is enhanced, which allows a flexural deformation of the support part 30 to be decreased in turning the support part 30. As a result, the turning movements of the X-ray generator 40 and X-ray detector 45 can accurately be maintained, and the weight of the X-ray CT apparatus 20 can be reduced. Particularly, the wobble of the X-ray generator 40 and the X-ray detector 45 due to the flexural deformation of the support structure is restrained, which allows a position shift to be restrained between the images sequentially obtained in turning the X-ray generator 40 and the X-ray detector 45. As a result, the accurate X-ray CT image can be obtained.

Specifically, the exterior part 32 includes a pair of arms 34 and 36 extending along the turning axis A and an arm base part 38. The arm 34 constitutes an X-ray generation part 40A of the support part 30 together with the X-ray generator 40, and the arm 36 constitutes an X-ray detection part 45A of the support part 30 together with the X-ray detector 45.

The pair of arms 34 and 36 is formed into a square tubular shape in which a leading end is closed, and the pair of arms 34 and 36 is arranged so as to extend along the turning axis A.

The arm base part 38 includes an intermediate body part 38a and bent parts 38b provided on both ends of the intermediate body part 38a. The intermediate body part 38a is formed into the square tubular shape extending in the direction orthogonal to the turning axis A, and the bent part 38b is formed into the square tubular shape that is bent in the direction along the turning axis A from the direction orthogonal to the turning axis A at an end of the intermediate body part 38a. The intermediate body part 38a and each of the bent parts 38b on both the ends thereof are connected to each other so as to form one square tube as a whole.

The pair of arms 34 and 36 is connected to both the ends of the arm base part 38, and the arms 34 and 36 are supported by the arm base part 38 in a parallel state in which the arms 34 and 36 are opposed to each other with the turning axis A interposed therebetween.

When the exterior part 32 is viewed as a whole, the pair of arms 34 and 36 and the arm base part 38 are formed into a continuous tubular U-shape (in this case, the square tubular shape). In the exterior part 32, a cavity is formed from the end of the arm 34 to the end of the arm 36 through the arm base part 38. The surface of the exterior part 32 may be painted.

The X-ray generator 40 is attached to the leading end of the arm 34, and the X-ray detector 45 is attached to the leading end of the arm 36.

The X-ray generator 40 includes an X-ray generation main body 41 and an X-ray regulating part 42. The X-ray generation main body 41 is constructed with an X-ray tube, and generates the X-ray. The X-ray regulating part 42 is provided in front of an X-ray irradiation direction in the X-ray generation main body 41, and regulates an X-ray irradiation region. The X-ray regulating part 42 is constructed with a plate-like member in which an opening is formed to regulate spread of the X-ray, and sometimes the X-ray regulating part 42 is called a collimator. The opening is formed into a slit shape or a substantially square shape having a predetermined size according to a mode of the X-ray CT photography. As to the plate-like member forming the opening, various configurations can be used according to an object region for the purpose of X-ray photography or CT photography. For example, one or plural openings are provided in one plate, the opening is formed by sliding and overlapping at least two plates, or the opening shape and an opening area can be changed by movably arranging at least two plates. For example, the opening regulates the X-ray such that the X-ray constitutes an X-ray cone beam.

In the example of FIG. 5, shielding plates 421 and 422 form an opening 425 that permits the X-ray to pass therethrough. Each of the shielding plates 421 and 422 is independently displaced in a Z-direction with respect to the X-ray generation main body 41. The shielding plates 421 and 422 come close to each other to be able to decrease a width in the Z-direction of the opening 425, and the shielding plates 421 and 422 separate from each other to be able to increase the width in the Z-direction of the opening 425. The shielding plates 421 and 422 can be displaced in the identical direction to change an X-ray irradiation direction with respect to the Z-direction, and the shielding plates 421 and 422 can also move to change both the X-ray irradiation direction and the width. The shielding plates 421 and 422 are displaced by a shielding plate drive mechanism provided with an actuator such as a motor. However, the shielding plate drive mechanism is not illustrated.

When the shielding plates 421 and 422 regulate the lengthwise passage of the X-ray, shielding plates 423 and 424 (not illustrated) that regulate the crosswise passage of the X-ray are also provided.

The shielding plates 423 and 424 are arranged in front of or at the back of the shielding plates 421 and 422 in the X-ray irradiation direction while being adjacent to the shielding plates 421 and 422, and the shielding plates 423 and 424 regulate the X-ray generating from an outgoing port 411 of the X-ray generation main body 41 in the crosswise direction intersecting the moving direction of the shielding plates 421 and 422. Since the independent displacements of the shielding plates 423 and 424 in the direction intersecting the Z-direction with respect to the X-ray generation main body 41 differ from those of the shielding plates 421 and 422 only in the direction, the description is omitted.

The X-ray generator 40 is attached to the leading end of the arm 34 at a position and with a posture such that the leading end of the arm 36 can be irradiated with the X-ray cone beam.

Specifically, a generator-side opening 35 is formed in an inward portion at the leading end of the arm 34. At this point, the generator-side opening 35 is formed into a square shape in the inward portion at the leading end of the arm 34. In accommodating the X-ray generator 40 in the arm 34, the X-ray generator 40 passes through the generator-side opening 35. Accordingly, the generator-side opening 35 is formed to a size through which the X-ray generator 40 can pass.

Through the generator-side opening 35 of the arm 34, the X-ray generator 40 is attached to the arm 34 on a deep side of the generator-side opening 35 while accommodated in the arm 34.

In the state in which the X-ray generator 40 is attached to the arm 34, the X-ray detector 45 is irradiated with the X-ray generated by the X-ray generator 40 through the generator-side opening 35.

For example, the X-ray detector 45 is constructed with a Flat panel Detector (FPD) or an X-ray Image Intensifier (I.I.) that has a two-dimensionally expanding detection surface.

The X-ray detector 45 is attached to the inward portion at the leading end of the arm 36 with the posture where the detection surface can be irradiated with the X-ray from the X-ray generator 40.

Specifically, a detector-side opening 37 is formed in the inward portion at the leading end of the arm 36 while opposed to the generator-side opening 35. At this point, the detector-side opening 37 is formed into the square shape in the inward portion at the leading end of the arm 36. The X-ray detector 45 is attached to the detector-side opening 37 in the arm 36 while accommodated in the detector-side opening 37, and the X-ray detector 45 is opposed to the generator-side opening 35. That is, the X-ray detector 45 is attached to the leading end of the arm 36 so as to close the detector-side opening 37. At this point, the detection surface of the X-ray detector 45 projects from the detector-side opening 37, and extends so as to expand in the whole of the detector-side opening 37.

Therefore, the X-ray generator 40 and the X-ray detector 45 are supported by the pair of arms 34 and 36 while opposed to each other in relation to the turning axis A. The X-ray cone beam is emitted from the X-ray generation main body 41 through the generator-side opening 35 while the spread of the X-ray is regulated by the X-ray regulating part 42. The X-ray cone beam reaches the detection surface of the X-ray detector 45 through the turning axis A and a vicinity of the turning axis A.

The wiring to the X-ray generator 40 and the X-ray detector 45 is routed through the space in the exterior part 32. An opening for work to attach the wiring and a heat radiation opening may be formed at proper positions of the exterior part 32.

A positioning light emitting part 34a is provided at the leading end of the arm 34 in order to emit positioning light. The positioning light emitting part 34a is constructed with a light emitting diode or an electric bulb, and emits a visible light. The positioning light emitting part 34a is attached to a leading end of the arm 34 (in this case, at a leading-end lateral position) with the posture in which the positioning light emitting part 34a emits the light toward the space between the X-ray generator 40 and the X-ray detector 45. The light emitted from the positioning light emitting part 34a is regulated so as to indicate a photography position of the X-ray generator 40 and X-ray detector 45, e.g. by a shielding plate in which a slit is formed, a lens or the like. As to the mode in which the light emitted from the positioning light emitting part 34a indicates the photography position, the light is aimed at the turning axis A, the light is aimed at a boundary of the photography region. The light may be emitted in a linear shape, a point shape, or a planar shape. A position where the positioning light emitting part 34a is attached is not limited to the leading end of the arm 34, but the positioning light emitting part 34a may be attached to another portion of the arm 34 or the arm 36.

The support part 30 includes a turning support shaft part 50 that is provided so as to extend onto the opposite sides to the X-ray generator 40 and X-ray detector 45 along the turning axis A.

That is, a cavity part 39 is formed along the turning axis A in the arm base part 38. In this case, an opening 38h opened about the turning axis A is formed in a front portion and rear portion of the intermediate portion in the extending direction of the arm base part 38. A cylindrical member 38e is fitted in the opening 38h, and fixed to the exterior part 32 by a screw. A cavity part 39 constituting a space expanding about the turning axis A is formed on an inner circumferential side of the cylindrical member 38e. A fixing flange 38f projecting toward the inner peripheral side extends in an inner circumferential portion of the cylindrical member 38e and in the intermediate portion of the direction of the turning axis A.

The turning support shaft part 50 includes a first turning support shaft part 52 and a second turning support shaft part 56.

As illustrated in FIG. 4, the first turning support shaft part 52 includes a disc-shaped part 53 in which a center is opened and a cylindrical part 54 that extends from the central opening of the disc-shaped part 53 to the side of one of principal surfaces (rear side) of the disc-shaped part 53. The first turning support shaft part 52 is formed into a hollow shape in which the central opening of the disc-shaped part 53 and the space in the cylindrical part 54 are continuously connected to each other.

The second turning support shaft part 56 includes a cylindrical part 57 and a fixing flange 58 that expands toward the outer circumferential side from one end (rear-side end) of the cylindrical part 57.

The other end (front-side end) of the cylindrical part 57 is coupled to the other end (rear-side end) of the cylindrical part 54 of the first turning support shaft part 52. At this point, the other end of the cylindrical part 57 is fitted in one end of the cylindrical part 54, whereby the cylindrical part 57 and the cylindrical part 54 are coupled to each other. The fixing flange 58 is coupled to a hollow rotating shaft part 186 of a turning drive part 180 (to be described).

The disc-shaped part 53 is screwed while overlapped with the fixing flange 38f of the cylindrical member 38e, thereby fixing the turning support shaft part 50 to the exterior part 32. At this point, the turning support shaft part 50 extends onto the opposite side to the pair of arms 34 and 36 along the turning axis A with respect to the exterior part 32. The turning support shaft part 50 is formed into the hollow shape as a whole. The internal space of the first turning support shaft part 52 and the internal space of the second turning support shaft part 56 are continuously connected to each other in the hollow shape.

The turning support shaft part 50 is rotatably supported by the first bearing 160 and the second bearing 165, whereby the support part 30 is rotatably supported so as to be rotatable about the turning axis A in a cantilever manner. The other end of the turning support shaft part 50 is coupled to the hollow rotating shaft part 186 of the turning drive part 180 such that the turning support shaft part 50 and the hollow rotating shaft part 186 cannot relatively be rotated, and the turning support shaft part 50 is rotated by the turning drive part 180 to rotate the support part 30 about the turning axis A. The X-ray generator 40 and the X-ray detector 45 are rotated about the turning axis A by rotating the support part 30 about the turning axis A, and plural pieces of X-ray projection data obtained by photographing an affected area from plural directions can be acquired in order to reconstruct the CT image.

An accommodation part 60 is provided in the cavity part 39. The accommodation part 60 is formed into a bottomed cylindrical shape, and at least part of the subject P can be accommodated in accommodation part 60. More specifically, the accommodation part 60 has a configuration in which a peripheral wall 61b is formed around a circular plate 61a. An opening is formed in a central portion of the circular plate 61a. A bottom plate 61c is attached to the accommodation part 60 so as to close the opening of the circular plate 61a. At least part of the accommodation part 60 needs to be provided in the cavity part 39. Accordingly, a deep-side portion or a front-side portion of the accommodation part 60 may project from the cavity part 39.

Part (for example, a hand tip Pb) of the subject P (particularly, the subject P is part of the patient and a portion that becomes the X-ray photography target, for example, an upper arm Pa) can be accommodated in the accommodation part 60 while the subject P is provided between the X-ray generator 40 and the X-ray detector 45.

Although the accommodation part 60 is accommodated in the cavity part 39, the accommodation part 60 is not fixed to the cylindrical member 38e. At this point, a center axis of the accommodation part 60 is aligned with the turning axis A, and the accommodation part 60 is supported by an accommodation part support part 62 in the non-rotatable manner while the accommodation part 60 is opened toward the space between the pair of arms 34 and 36.

The accommodation part support part 62 includes an attaching member 63, a first accommodation part support shaft part 64, and a second accommodation part support shaft part 65.

The attaching member 63 includes a disc-shaped part 63a in which a center is opened and a cylindrical part 63b that extends from the central opening of the disc-shaped part 63a to the side of one of principal surfaces (rear side) of the disc-shaped part 63a.

The first accommodation part support shaft part 64 is formed into a cylindrical shape. One end (front-side end) of the first accommodation part support shaft part 64 is coupled to the end of the cylindrical part 63b. In this case, one end (front-side end) of the first accommodation part support shaft part 64 is coupled to the end of the cylindrical part 63b through an inside annular member 167 of a second bearing 165 (to be described).

The second accommodation part support shaft part 65 is formed into a round bar shape. One end (front-side end) of the second accommodation part support shaft part 65 is coupled to the other end (rear-side end) of the first accommodation part support shaft part 64. In this case, one end (front-side end) of the second accommodation part support shaft part 65 is coupled to the other end (rear-side end) of the first accommodation part support shaft part 64 while inserted in the other end (rear-side end) of the first accommodation part support shaft part 64.

One end (front-side end) of the accommodation part support part 62 is fixed to an outward surface of the circular plate 61a of the accommodation part 60, whereby the accommodation part support part 62 is supported with the posture in which the accommodation part support part 62 extends toward the opposite side to the opening of the accommodation part 60. The accommodation part support part 62 is provided through the internal space of the turning support shaft part 50 and the internal space of the hollow rotating shaft part 186 of the turning drive part 180 while being relatively rotatable with respect to the turning support shaft part 50. The other end (rear-side end) of the accommodation part support part 62 is fixed to the turning support base part 150 while projecting outward from the hollow rotating shaft part 186, which allows the accommodation part 60 to be supported at a constant position with a constant posture in the non-rotatable manner in the cavity part 39.

Preferably the cavity part 39 has the opening shape as large as possible with in the range in which the exterior part 32 keeps the supporting function. The opening of the accommodation part 60 is formed as large as possible within the range in which the accommodation part 60 can be accommodated in the cavity part 39.

In this case, the accommodation part 60 is supported in non-rotatable manner. Alternatively, the accommodation part 60 may rotatably be supported. In this case, the accommodation part 60 is relatively rotatably supported by the support part 30, but the accommodation part 60 is not driven even if the support part 30 rotates. That is, preferably the accommodation part 60 is kept in the non-rotating state.

In the support part 30 of the preferred embodiment, the turning support shaft part 50 extending in the Z-direction is coupled to the arm base part 38, and the arms 34 and 36 extend from the arm base part 38 to the Z-direction opposite to the turning support shaft part 50, whereby the space where the subject P is positioned can be formed between the arms 34 and 36.

The support part 30 has the U-shape as a whole in order to achieve the simplification and weight reduction of the support part 30. The U-shape is not the strict U-shape, but the shape may be a C-shape, and a shape in which the pair of arms extends in a parallel manner at right angle from both the ends of the arm base part. That is, the support part 30 is constructed with the arm base part 38 and the arms 34 and 36. The arm base part 38 is formed into either the linear shape or the curved shape, and extends substantially in the direction orthogonal to the Z-direction. The arms 34 and 36 are formed into either the linear shape or the curved shape, and extend substantially in the direction along the Y-direction. The coupling portion between the arm base part 38 and each of the arms 34 and 36 may be curved and smoothly be coupled or have a clear angle. And all of these shapes formed by the arm base part 38 and the arms 34 and 36 are collectively called the U-shape.

3. Structure of Base 3.1. Schematic Structure of Base

As illustrated in FIGS. 1, 2, and 5, the base 100 supports the support part 30 and the accommodation part 60. The base 100 includes a seat 102, an XYZ-direction moving mechanism 110, and a turning support base part 150.

The seat 102 constitutes a base portion provided below the X-ray CT apparatus 20. The seat 102 has the expansion to an extent to which the X-ray CT apparatus 20 can be supported with a constant posture so as not to be tilted in the planar manner. The seat 102 may have a structure in which plural frames are combined or a plate-like structure.

Wheels 109 are provided below the seat 102 as rolling elements that can roll on a floor. The wheels 109 are provided at four corners in the lower portion of the seat 102. The user of the X-ray CT apparatus 20 pushes the X-ray CT apparatus 20, which allows the X-ray CT apparatus 20 to move on a floor surface.

Thus, the X-ray CT apparatus 20 can easily be moved by providing the wheels 109. The X-ray CT apparatus 20 can easily be moved in combination with the weight reduction of the support part 30.

A stopping state of the X-ray CT apparatus 20 may be maintained by providing a well-known lock mechanism that stops the rolling of the wheel in at least one of the wheels 109.

The XYZ-direction moving mechanism 110 is provided on the seat 102. The XYZ-direction moving mechanism 110 moves the turning support base part 150 and each part (including the support part 30) directly or indirectly supported by the turning support base part 150 in the Z-direction parallel to the turning axis A, the X-direction orthogonal to the Z-direction in a horizontal plane, and the Y-direction that is of the vertical direction orthogonal to both the Z-direction and the X-direction with respect to the seat 102.

The turning support base part 150 is supported so as to be movable in the XYZ-direction by the XYZ-direction moving mechanism 110. The turning support base part 150 can support the turning support shaft part 50 and the accommodation part support part 62 and the like.

The support part 30 is supported by the turning support base part 150, whereby the support part 30 and the turning support base part 150 are supported while being movable in the XYZ-direction. The accommodation part 60 is also directly or indirectly supported by the turning support base part 150, and the accommodation part 60 and the support part 30 are supported while being movable in the XYZ-direction.

The base 100 includes a cover 104 that covers each part. The cover 104 is made of resin or metal, and the cover 104 protects each part such that the part is not exposed to the outside.

In this case, the cover 104 includes a cover body 104a and a front cover 104b. The cover body 104a covers surroundings and an upper portion of the XYZ-direction moving mechanism 110, and is fixed to a constant position with respect to the seat 102. In the cover body 104a, an opening is formed in the portion corresponding to the support part 30, and the front cover 104b is provided so as to close the opening. Although not illustrated, the front cover 104b is fixed to a Z-direction moving plate that moves in the Z-direction in the XYZ-direction moving mechanism 110, and the front cover 104b closes the opening of the cover body 104a while moving only in the Z-direction together with the Z-direction moving plate.

An opening in which the turning support shaft part 50 is inserted is formed in the front cover 104b. In the turning support shaft part 50, a shaft cover 104c is attached to the surrounding of the portion passing through the front cover 104b. The shaft cover 104c is fixed to the base plate 152. An opening is formed in the center of the shaft cover 104c, and the turning support shaft part 50 pierces the opening. Because the shaft cover 104c is mechanically separated from the turning support shaft part 50, the shaft cover 104c is not rotated by following the turning support shaft part 50. Due to the above fixing relationship, the shaft cover 104c moves in the Z-direction together with the front cover 104b, and the shaft cover 104c can close the opening formed in the front cover 104b while moving in the X-direction and the Y-direction with respect to the front cover 104b.

Display manipulation panels 106 and 107 are provided in a side portion and a rear portion in the upper side portion of the base 100, and a CT image processing unit (not illustrated) is provided in the base 100.

For example, the display manipulation panels 106 and 107 are constructed with a touch panel and the like. The display manipulation panels 106 and 107 are used as a display device displaying pieces of information on the CT photography and an input device inputting various instructions concerning the CT photography. The display device and the input device may separately be incorporated.

The CT image processing unit is a processing control unit that is constructed with a general microcomputer including a CPU, a ROM, a RAM and the like. According to previously-stored software and various instructions inputted by the display manipulation panels 106 and 107, the CT image processing unit performs operation control of the XYZ-direction moving mechanism 110, operation control of the turning drive part 180 during the CT photography, and calculation processing of reconstructing the photography target CT image based on the electric signal obtained by the X-ray detector 45 in photography. The photographed CT image may be displayed on the display manipulation panels 106 and 107, or displayed on another display part through a wired or wireless communication circuit. The photographed CT image may be recorded in recording mediums such as a magnetic recording medium, an optical recording medium, a flash memory and the like.

3.2. Support Structure for Support Part and Accommodation Part

A support structure for the support part 30 and accommodation part 60 will specifically be described with reference to FIGS. 2 to 6.

As described above, the turning support base part 150 is movably supported by the XYZ-direction moving mechanism 110.

The turning support base part 150 includes a base plate 152, a rear portion support part 154, and a bearing support part 156.

The base plate 152 is supported with a horizontal posture at a position above the XYZ-direction moving mechanism 110.

The rear portion support part 154 is formed into a plate shape as a whole. The rear portion support part 154 may be constructed with one plate-like member or plural plate-like members. FIG. 4 illustrates the rear portion support part 154 having the configuration in which the plate-like member is attached to a back side of another plate-like member in which a hole is made in the center so as to close the hole, and FIG. 5 illustrates the rear portion support part 154 that is simplified as one plate-like member.

The rear portion support part 154 is fixed to the rear portion of the base plate 152 with the posture orthogonal to the turning axis A. The rear portion support part 154 may be fixed to the base plate 152 with another bracket interposed therebetween, or directly be fixed to the base plate 152.

The bearing support part 156 is fixed to the base plate 152 with a constant posture at a constant position where the bearing support part 156 is separated from the rear portion support part 154 and located closer onto the side (that is, the front side) of the support part 30 along the turning axis A. The bearing support part 156 is formed into the annular shape surrounding the turning axis A. The bearing support part 156 may directly be fixed to the base plate 152 or the rear portion support part 154, or be fixed to the base plate 152 or the rear portion support part 154 with another bracket interposed therebetween.

A first bearing 160 is supported in an inner circumferential portion of the bearing support part 156. In the first bearing 160, an outside annular member 161 and an inside annular member 162 are coupled to each other in the relatively rotatable manner while a rolling element such as a circular cylinder and a ball is interposed therebetween. The outside annular member 161 is fixed to the inside of the bearing support part 156 in the relatively non-rotatable manner, and the inside annular member 162 is fixed to the outer circumferential portion of the turning support shaft part 50 in the relatively non-rotatable manner. At this point, the inside annular member 162 is fixed to the outer circumference at the end of the cylindrical part 54 in the turning support shaft part 50.

The turning support shaft part 50 is rotatably supported by the first bearing 160 at the position distant from the turning drive part 180 along the turning axis A.

A second bearing 165 is provided at a position distant from the first bearing 160 on the side (that is, the front side) of the support part 30 along the turning axis A. In the second bearing 165, an outside annular member 166 and an inside annular member 167 are coupled to each other in the relatively rotatable manner while a rolling element such as a circular cylinder and a ball is interposed therebetween. The outside annular member 166 is fixed to the turning support shaft part 50 in the relatively non-rotatable manner. At this point, the outside annular member 166 is fixed while the inner circumferential side of the outside annular member 166 projects toward the front side of the first turning support shaft part 52 in the turning support shaft part 50, more specifically, the principal surface on the front side of the disc-shaped part 53. The inside annular member 167 is fixed to the accommodation part support part 62 in the relatively non-rotatable manner. That is, the accommodation part support part 62 rotatably supports the turning support shaft part 50 by supporting the second bearing 165, and the accommodation part support part 62 is also used as one element of the turning support base part 150 in this point.

The turning support shaft part 50 is separated from the turning drive part 180 along the turning axis A by the second bearing 165, and the turning support shaft part 50 is rotatably supported at the position distant from the first bearing 160.

Thus, the turning support shaft part 50 is rotatably supported above the seat 102 by the first bearing 160 and second bearing 165 of the turning support base part 150, whereby the turning support base part 150 rotatably supports the support part 30 in the cantilever manner.

Thus, the turning support shaft part 50 is rotatably supported by the first bearing 160 and the second bearing 165, whereby a moment load generated by the turning support shaft part 50 arranged along the turning axis A can be restrained from acting directly on the turning drive part 180, and the wobble of the actual rotating axis of the turning support shaft part 50 can be prevented.

The mode in which the turning support shaft part 50 is rotatably supported is conceivable in many ways. For example, a sliding bearing and a rolling bearing may be used as the bearing. For the rolling bearing, a ball bearing and a roller bearing may be used as the bearing. Preferably a cross roller bearing that has a resistance to loads from various directions such as a radial load and an axial load is used as the bearing. Therefore, the support part 30 can rotatably be supported with high accuracy.

The accommodation part support part 62 of the accommodation part 60 reaches the rear portion support part 154 through the turning support shaft part 50 and the turning drive part 180, and is fixed to the rear portion support part 154 in the relatively non-rotatable manner. Therefore, the accommodation part support part 62 and the accommodation part 60 are supported in the non-rotatable manner in the cavity part 39.

At this point, in the turning support base part 150, a rotating position detector 170 and a rotation brake 175 are provided at positions around the turning support shaft part 50.

The rotating position detector 170 includes a rotating position detecting shaft 172 and a detector 173. The rotating position detecting shaft 172 is coupled to the turning support shaft part 50 through a rotation transmission mechanism 171 such as a gear, and the rotating position detecting shaft 172 can be rotated in synchronization with the turning support shaft part 50. The detector 173 such as an encoder detects a rotation angle of the rotating position detecting shaft 172.

The rotation brake 175 includes a braking shaft 177 and a brake 178. The braking shaft 177 is coupled to the turning support shaft part 50 while a rotation transmission mechanism 176 such as the gear is interposed therebetween, and the braking shaft 177 can be rotated in synchronization with the turning support shaft part 50. The brake 178 can regulate the rotation of the braking shaft 177. For example, an electromagnetic brake can be used as the brake 178. The rotation angle of the support part 30 is detected by the rotating position detector 170. If the support part 30 is determined to reach a predetermined amount or more, the rotation brake 175 stops the rotation of the braking shaft 177, and therefore stops the rotation of the support part 30.

Therefore, for example, in the case where the user manually rotates the support part 30, the support part 30 can be restrained from excessively rotating.

3.3. Rotating Structure of Support Part

As illustrated in FIGS. 2 to 5, the support part 30 and the turning support shaft part 50 are rotated by the turning drive part 180 constructed with a hollow motor 182.

The hollow motor 182 includes a hollow main body 184 and the hollow rotating shaft part 186. The hollow main body 184 is formed into an annular shape. The hollow rotating shaft part 186 is formed into an annular shape, and rotatably supported in the hollow main body 184. Part of an armature and a magneton are incorporated in the hollow main body 184, another part of the armature and the magneton are incorporated in the hollow rotating shaft part 186, and the hollow rotating shaft part 186 is rotated with respect to the hollow main body 184 by the action of the armature and the magneton. The hollow motor 182 is also configured as a motor that can control the rotation angle of a servo motor. The rotation angle (the rotating direction and the rotating amount) of the hollow motor 182 is controlled under the control of the processing control unit.

The hollow main body 184 of the hollow motor 182 is fixed to the turning support base part 150. At this point, the hollow main body 184 is fixed to the base plate 152 by fixing an annular end face on the rear side of the hollow main body 184 to the rear portion support part 154. The hollow main body 184 may be fixed to the base plate 152 with another bracket interposed therebetween. More preferably a direct-drive hollow motor can be used as the hollow motor.

The hollow rotating shaft part 186 projects on one side (front side) of the hollow main body 184, and the rear end of the turning support shaft part 50 is coupled to an end face of the hollow rotating shaft part 186 in the relatively non-rotatable manner by a screw.

The hollow rotating shaft part 186 is rotated by driving the turning drive part 180, whereby the turning support shaft part 50 and the support part 30 are rotated while rotating directions and rotating amounts of the turning support shaft part 50 and support part 30 are controlled.

3.4. XYZ-Direction Moving Mechanism

The XYZ-direction moving mechanism 110 will be described with reference to FIGS. 2, 5, and 7.

The XYZ-direction moving mechanism 110 includes a Y-direction moving mechanism 120 and a ZX-direction moving mechanism 130. The processing control unit performs the control in each moving direction of the XYZ-direction moving mechanism 110.

The Y-direction is a direction along the vertical direction (up and down), the X-direction is a direction along the turning axis A in the horizontal direction turning axis A, and the Z-direction is a direction along the horizontal direction orthogonal to both the X-direction and the Y-direction.

The Z-direction is identical to the axial direction of the turning axis A, and is set to the horizontal direction in the examples of FIGS. 2, 5, and 7. Both the X-direction and the Y-direction are orthogonal to the Z-direction, the Y-direction is set to the vertical direction in the examples of FIGS. 2, 5, and 7, and the X-direction is set to the direction along the horizontal direction.

The Y-direction moving mechanism 120 can elevate the turning support base part 150 along the Y-direction, and the ZX-direction moving mechanism can move the turning support base part 150 along the Z-direction and X-direction together with the Y-direction moving mechanism 120.

More specifically, the ZX-direction moving mechanism 130 is provided on the seat 102.

The ZX-direction moving mechanism 130 includes a Z-direction moving mechanism 132 and an X-direction moving mechanism 142. The Z-direction moving mechanism 132 is provided on the seat 102, and the X-direction moving mechanism 142 is provided on the Z-direction moving mechanism 132.

The Z-direction moving mechanism 132 includes a pair of Z-direction guides 133, a Z-direction drive part 134, and a Z-direction moving plate 135.

The pair of Z-direction guides 133 is constructed with a linear guide, and arranged on the seat 102 with a parallel posture along the Z-direction. The Z-direction moving plate 135 is supported by the pair of Z-direction guides 133 so as to be reciprocal in the Z-direction with respect to the seat 102.

The Z-direction drive part 134 is constructed with a linear drive mechanism including a motor and a ball screw, a linear motor, and a fluid cylinder. The Z-direction drive part 134 is provided between the seat 102 and the Z-direction moving plate 135 so as to move the Z-direction moving plate 135 in the Z-direction with respect to the seat 102.

For example, a guided member fixed to a Z-direction moving plate can be moved in the Z-direction by the rotation of the ball screw of the Z-direction drive part 134.

The X-direction moving mechanism 142 includes a pair of X-direction guides 143, an X-direction drive part 144, and an X-direction moving plate 145.

The pair of X-direction guides 143 is constructed with a linear guide, and arranged on the Z-direction moving plate 135 with a parallel posture along the X-direction. The X-direction moving plate 145 is supported by the pair of X-direction guides 143 so as to be reciprocal in the X-direction with respect to the Z-direction moving plate 135.

The X-direction drive part 144 is constructed with a linear drive mechanism including a motor and a ball screw, a linear motor, and a fluid cylinder. The X-direction drive part 144 is provided between the Z-direction moving plate 135 and the X-direction moving plate 145 so as to move the X-direction moving plate 145 in the X-direction with respect to the Z-direction moving plate 135.

For example, a guided member fixed to an X-direction moving plate can be moved in the X-direction by the rotation of the ball screw of the X-direction drive part 144.

The Y-direction moving mechanism 120 provided in the X-direction moving plate 145 is maintained by the Z-direction moving mechanism 132 and the X-direction moving mechanism 142 so as to be movable in a ZX two-dimensional plane.

The Y-direction moving mechanism 120 includes a guide rod 121, a drive rod 125, an elevating guide 122, and an elevating drive part 126.

The guide rod 121 and the drive rod 125 are long members provided in a hung manner in the base plate 152.

The elevating guide 122 is provided on the X-direction moving plate 145, and supports the guide rod 121 so as to be able to elevate the guide rod 121. At this point, the elevating guide 122 is vertically formed as a member including a cylindrical space in which the guide rod 121 can be inserted. The elevating guide 122 is erected on the X-direction moving plate 145 with the vertical posture. A guide roller 122a (see FIG. 5) is rotatably supported in the elevating guide 122. When the guide rod 121 is inserted in the elevating guide 122, the guide roller 122a is pressed against the outer peripheral surface of the guide rod 121. The guide rod 121 can be elevated in the elevating guide 122 while the guide roller 122a is driven by the guide rod 121.

The elevating drive part 126 elevates the turning support base part 150 including the base plate 152 by elevating the drive rod 125.

The elevating drive part 126 includes a motor 126a and a transmission mechanism 126b that converts rotation movement of the motor 126a into linear movement. For example, a mechanism in which a rack gear and a pinion gear are combined or a ball screw mechanism can be used as the transmission mechanism 126b. Alternatively, a structure provided with a fluid cylinder may be used as the elevating drive part.

The guide rod 121 is guided by the elevating guide 122 so as to be able to be elevated, and the elevating drive part 126 elevates the drive rod 125, thereby elevating the turning support base part 150, the support part 30, and the accommodation part 60.

The combination of the X-direction moving mechanism, Y-direction moving mechanism, and Z-direction moving mechanism of the XYZ-direction moving mechanism is not limited to the above example, but the moving mechanism can arbitrarily be provided on the base side or the turning support base part side. One or two moving mechanisms in the XYZ-direction may be eliminated, or all the moving mechanisms in the XYZ-direction may be eliminated.

4. Operation and Effect

In the X-ray CT apparatus 20, in the case where the subject P (e.g., the upper arm Pa) of the patient is photographed, the arm that is of the subject P of the patient is provided between the X-ray generator 40 and the X-ray detector 45 along the turning axis A (see FIG. 1). According to the position of the portion that becomes the subject P of the patient and a height of the patient, the XYZ-direction moving mechanism 110 adjusts the positions of the X-ray generator 40 and X-ray detector 45 that are supported by the support part 30 such that the subject P is provided along the turning axis A.

While the subject P is kept at a constant position, the X-ray generator 40 and the X-ray detector 45 are turned about the turning axis A by driving the turning drive part 180. In the X-ray CT apparatus 20, the X-ray generator 40 and the X-ray detector 45 are stopped in the direction along the turning axis A during the rotation for the X-ray CT photography. That is, each of the X-ray generator 40 and the X-ray detector 45 is not displaced in the Z-direction during the X-ray CT photography, but turns on the XY-plane expanding in the X-direction and the Y-direction. Alternatively, the X-ray CT photography are continuously performed at plural places, the X-ray CT photography is completed at a certain position on the Z-direction, and then the X-ray CT photography may be performed at another position on the Z-direction by displacing the Z-direction moving plate. Based on signals reflecting plural pieces of projection data obtained by the X-ray detector 45, the calculation is performed in order to reconstruct the image, and three-dimensional image data of the photographed region is generated to obtain the CT image.

In the case where the Z-direction moving plate is displaced to perform the X-ray CT photography at a certain position on the Z-direction after the X-ray CT photography is completed at another position on the Z-direction, the obtained pieces of three-dimensional image data at the plural places are joined while matched with the arrangement of the actual photographed region, and one three-dimensional image data may be generated.

In the X-ray CT apparatus 20 having the above configuration, the support part 30 includes an exterior part 32 made of the carbon fiber reinforced plastic, and the X-ray generator 40 and the X-ray detector 45 are supported by the exterior part 32 while opposed to each other. The weight of the carbon fiber reinforced plastic itself is light, and the space is formed in the exterior part 32, so that the weight reduction of the support part 30 including the exterior part 32 can be achieved. As a result of the weight reduction of the support part 30, the first bearing 160 and second bearing 165 that rotatably support the support part 30 and the structural portion that supports the first bearing 160 and the second bearing 165 can have proper strength according to the light support part 30, and the weight of the structural portion that supports the first bearing 160 and the second bearing 165 can be reduced. Therefore, the weight of the X-ray CT apparatus 20 can be reduced.

The carbon fiber reinforced plastic has excellent strength, and the structural portion supporting the X-ray generator 40 and the X-ray detector 45 is formed into the shape constituting the exterior part 32, which allows the support part 30 having the excellent rigidity to be made. The weight of the support part 30 including the exterior part 32 is reduced, and the rigidity of the support part 30 is enhanced, which allows the restraint of the actual wobble of the turning axis in turning the X-ray generator 40 and X-ray detector 45.

Thus, the actual wobble of the turning axis for the X-ray generator 40 and X-ray detector 45 can be restrained, and the weight of the X-ray CT apparatus 20 can be reduced.

Particularly, for the horizontally-provided turning axis A, the gravity application directions of the X-ray generator 40 and the X-ray detector 45 vary about the horizontal turning axis A. For example, when the X-ray generator 40 or the X-ray detector 45 is located above the turning axis A, the gravity of the X-ray generator 40 or X-ray detector 45 is applied in the direction coming close to the turning axis A.

On the other hand, when the X-ray generator 40 or the X-ray detector 45 is located below the turning axis A, the gravity of the X-ray generator 40 or X-ray detector 45 is applied in the direction receding from the turning axis A. Therefore, the wobble of the turning axis is easily generated when the turning axis A is horizontally provided.

In the structure in which the base 100 supports the support part 30 such that the turning axis A is horizontal, the effect that the weight reduction of the X-ray CT apparatus 20 is achieved while the wobble of the turning axis for the X-ray generator 40 and X-ray detector 45 is restrained can significantly be exerted using the structure in which the support part 30 includes the exterior part 32 made of carbon fiber reinforced plastic. Particularly, in the case where the support part is formed into the shape in which the pair of arms extends in parallel at right angle with respect to both the ends of the arm base part, flexure and strain of each arm can effectively be restrained to achieve significant effects.

Alternatively, the above structure may be applied to an X-ray CT apparatus in which the X-ray generator and the X-ray detector are turned about the turning axis along the vertical direction.

The exterior part 32 includes the pair of arms 34 and 36 extending along the turning axis A, and the X-ray generator 40 and the X-ray detector 45 are supported by the pair of arms 34 and 36 while opposed to each other, so that the X-ray CT apparatus can be made compact and light compared with an X-ray CT apparatus (what is called a gantry type X-ray CT apparatus) in which the X-ray generator and the X-ray detector are supported by an annular gantry.

In the gantry type X-ray CT apparatus, the annular exterior part constituting the gantry may be made of the carbon fiber reinforced plastic.

As described above, because of the light support part 30, even in the structure in which the support part 30 is supported in the cantilever manner by the turning support base part 150, the simplification and weight reduction of the structure supporting the light support part 30 can be achieved using the structure having the strength corresponding to the light support part 30.

The generator-side opening 35 to which the X-ray generator 40 is attached while accommodated therein is formed in one of the pair of arms 34 and 36, and the detector-side opening 37 to which the X-ray detector 45 is attached while accommodated therein is formed in the other of the pair of arms 34 and 36. Therefore, protrusions of the X-ray generator 40 and the X-ray detector 45 are decreased while the X-ray generator 40 and the X-ray detector 45 are attached to the exterior part 32, and the compact structure can be achieved.

The X-ray CT apparatus 20 includes the Y-direction moving mechanism 120 and the ZX-direction moving mechanism 130 that moves the Y-direction moving mechanism 120 in the ZX-direction. Therefore, the support part 30, the X-ray generator 40, and the X-ray detector 45 can three-dimensionally be moved, and the degree of freedom of an X-ray irradiation field of the X-ray generator 40 can be enhanced.

Because of the light support part 30, the support part 30 places a small burden on the Y-direction moving mechanism 120 and the ZX-direction moving mechanism 130. When the support part 30 is made of metal like a conventional one, the X-ray CT apparatus is too heavy to be manually carried. On the other hand, in the structure of the preferred embodiment, the light X-ray CT apparatus 20 that is manually carried by one person can be provided.

The ZX-direction moving mechanism 130 moves the turning support base part 150 in the ZX-direction together with the Y-direction moving mechanism 120, so that the miniaturization and weight reduction can be achieved in the portion that is elevated by the Y-direction moving mechanism 120. As a load concerning the elevating drive is decreased in the Y-direction moving mechanism 120, the miniaturization and weight reduction of the Y-direction moving mechanism 120 can be achieved.

The hollow motor 182 is used as the turning drive part 180, and the turning support shaft part 50 is directly driven by the hollow motor 182. Therefore, for example, compared with the structure in which the rotation drive force of the motor laterally provided on the side of the turning support shaft part is transmitted through an annular belt and a pulley, the turning angles of the turning support shaft part 50 and the support part 30 can accurately be controlled, and the turning support shaft part 50 and the support part 30 can compactly be made.

The wobble of the turning axis A can be effectively restrained because the turning support shaft part 50 is rotatably supported at the position distant from the turning drive part 180 along the turning axis A while the first bearing 160 and the second bearing 165 are interposed therebetween.

Alternatively, for example, another structure in which the rotation drive force of the motor provided around the turning support shaft part is transmitted through the annular belt, the pulley, and a gear may be used as the turning support shaft part.

Since the first bearing 160 and the second bearing 165 are provided while separated from each other along the turning axis A, the turning support shaft part 50 can be supported at the positions separated from each other along the turning axis A, and the wobble of the turning axis A can effectively be restrained.

The turning support shaft part may rotatably be supported by one bearing or at least three bearings. In addition to the horizontal direction, the turning support shaft part may be supported while tilted by about 20 degrees with respect to the horizontal direction, or the turning support shaft part may be supported at a variable tilt angle including the horizontal direction.

The cavity part 39 is formed around the turning axis A in the arm base part 38 of the support part 30, so that the subject P (e.g., the upper arm Pa) can effortlessly be provided between the X-ray generator 40 and the X-ray detector 45 while avoiding an interference of the subject P (e.g., the hand tip Pb) and the support part 30. Therefore, necessity to force the subject P that is of the patient to take an unusual posture is eliminated.

Additionally, the accommodation part 60 is provided such that at least part of the cavity part 39 is accommodated in the cavity part 39, and the accommodation part 60 is relatively rotatable with respect to the support part 30 (in this case, the accommodation part 60 is supported in the non-rotatable manner). Therefore, contact of the subject P with the turning region of the support part 30 can be avoided.

In the accommodation part 60, the accommodation part support part 62 is fixed to the turning support base part 150 through the turning support shaft part 50 and the hollow rotating shaft part 186 of the hollow motor 182, so that the accommodation part 60 can be fixed by a simple and compact structure.

While the invention has been shown and described in detail, the foregoing description is in all aspects illustrative and not restrictive. It is therefore understood that numerous modifications and variations can be devised without departing from the scope of the invention.

What is claimed is:

1. An X-ray CT apparatus comprising:
   an X-ray generator;
   an X-ray detector;
   a support part that comprises an exterior part comprising carbon fiber reinforced plastic, wherein said support part supports said X-ray generator and said X-ray detector, wherein said X-ray generator and said X-ray detector are opposed to each other; and
   a base that rotatably supports said support part such that said X-ray generator and said X-ray detector turn about a turning axis, wherein
   said base supports said support part such that said turning axis is horizontal, said exterior part includes a pair of arms, and an arm base part that supports said pair of arms in a parallel state, said pair of arms being opposed to each other in relation to said turning axis, said exterior part is formed into a tubular shape in which said pair of arms and said arm base part are continuously provided so as to form a U-shape,
   said X-ray generator is attached to one of said pair of arms in an accommodated state, said X-ray detector is attached to the other of said pair of arms in an accommodated state,
   a turning support shaft part is attached to said exterior part so as to extend onto an opposite side to said pair of arms along said turning axis; wherein said support part includes said turning support shaft part that is provided on an opposite side to said X-ray generator and said X-ray detector along said turning axis.

2. The X-ray CT apparatus according to claim 1, wherein said exterior part includes said pair of arms extending along said turning axis, said X-ray generator and said X-ray detector are supported by said pair of arms.

3. The X-ray CT apparatus according to claim 2, wherein said base includes a seat and a turning support base part that rotatably supports said turning support shaft part above said seat to support said support part in a cantilever manner.

4. The X-ray CT apparatus according to claim 3, further comprising:
   a Y-direction moving mechanism that moves said turning support base part in a Y-direction along a vertical direction; and
   a ZX-direction moving mechanism that moves said turning support base part in a Z-direction along said turning axis and an X-direction orthogonal to both said Y-direction and said Z-direction together with said Y-direction moving mechanism.

5. The X-ray CT apparatus according to claim 3, further comprising
   a turning drive part that is constructed with a hollow motor including a hollow rotating shaft part, wherein
   said turning drive part is fixed to said turning support base part, said hollow rotating shaft part is coupled to said turning support shaft part, and
   said turning support shaft part is rotatably supported with a bearing interposed therebetween at a position separated from said turning drive part along said turning axis.

6. The X-ray CT apparatus according to claim 5, wherein a
   plurality of bearings are provided, and
   said plurality of bearings are provided along said turning axis while separated from each other.

7. The X-ray CT apparatus according to claim 5, further comprising:
   an accommodation part that is provided on said turning axis while opened towards said pair of arms, at least a part of a subject being able to be accommodated in said accommodation part; and
   an accommodation part support part that is arranged through an internal space of said turning support shaft part, one end of said accommodation part support part being fixed to said accommodation part while the other end is fixed to said turning support base part, wherein
   a cavity part is formed along said turning axis in said arm base part, and said turning support shaft part is formed into a hollow shape.

8. The X-ray CT apparatus according to claim 1, wherein a generator-side opening is formed in one of said pair of arms in order to accommodate said X-ray generator in said generator-side opening, a detector-side opening is formed in the other of said pair of arms while opposed to said generator-side opening, said X-ray detector in an accommodated state being attached to said detector-side opening.

* * * * *